(12) United States Patent
Pedrazzini

(10) Patent No.: US 8,926,902 B2
(45) Date of Patent: Jan. 6, 2015

(54) ALIQUOTING APPARATUS FOR BIOLOGICAL MATERIAL CONTAINERS

(75) Inventor: Gianandrea Pedrazzini, Paradiso (CH)

(73) Assignee: Inpeco Holding Ltd., Valletta (MT)

( * ) Notice: Subject to any disclaimer, the term of this patent is extended or adjusted under 35 U.S.C. 154(b) by 485 days.

(21) Appl. No.: 13/256,880

(22) PCT Filed: Mar. 12, 2010

(86) PCT No.: PCT/EP2010/053228
§ 371 (c)(1),
(2), (4) Date: Oct. 12, 2011

(87) PCT Pub. No.: WO2010/105992
PCT Pub. Date: Sep. 23, 2010

(65) Prior Publication Data
US 2012/0058010 A1    Mar. 8, 2012

(30) Foreign Application Priority Data

Mar. 16, 2009 (IT) .............................. MI2009A0398

(51) Int. Cl.
*G01N 15/06* (2006.01)
*G01N 33/00* (2006.01)
*G01N 33/48* (2006.01)
*G01N 35/04* (2006.01)
*G01N 35/00* (2006.01)
*G01N 35/10* (2006.01)

(52) U.S. Cl.
CPC ...... *G01N 35/04* (2013.01); *G01N 2035/00861* (2013.01); *G01N 2035/0467* (2013.01); *G01N 2035/1032* (2013.01)
USPC ................ 422/65; 422/68.1; 422/64; 422/66; 422/67; 422/81; 436/43; 436/174; 436/180

(58) Field of Classification Search
CPC ....... G01N 21/00; G01N 31/00; G01N 33/00; G01N 15/06; G01N 35/00; G01N 1/00
USPC .............. 422/50, 68.1, 63, 64, 65, 66, 67, 81; 436/43, 174, 180
See application file for complete search history.

(56) References Cited

U.S. PATENT DOCUMENTS

| | | | |
|---|---|---|---|
| 5,941,366 A | 8/1999 | Quinlan et al. | |
| 2004/0241043 A1* | 12/2004 | Sattler | 422/64 |
| 2008/0069730 A1 | 3/2008 | Itoh | |
| 2013/0236360 A1* | 9/2013 | Gunji | 422/63 |

FOREIGN PATENT DOCUMENTS

| | | |
|---|---|---|
| EP | 0 243 915 A2 | 11/1987 |
| WO | WO 99/28724 A1 | 6/1999 |

\* cited by examiner

*Primary Examiner* — Brian J Sines
(74) *Attorney, Agent, or Firm* — Birch, Stewart, Kolasch & Birch, LLP

(57) ABSTRACT

An automatic apparatus is described, which is suitable for the withdrawal of portions of biological material from a parent test tube (1), mobile in a conveyor (6) of a test tube transport plant by means of transport devices (8) of single test tubes, to be loaded in one or more child test tubes (2) countermarked beforehand with suitable identification means and to be sent to different biological material analysis instruments interfaced to said transport plant. Said apparatus comprises a work bench (5) which provides a first lane (9) for stocking and filling of transport devices (8) with empty child test tubes (2), a second lane (10) for stocking parent test tubes (1), said lanes (9, 10) being selectively joined in such a way to consent the sending of single parent test tubes (1) with a predefined number of child test tubes (2) subsequently assigned to be filled with biological material drawn from the parent test tube (1) in a work point (11), and a return third lane (12) of parent test tubes (1) and child test tubes (2) filled with portions of biological material drawn from parent test tubes (1), said lanes (9, 10, 12) joining to a conveyor (6) suitable for the transport of test tubes to and from subsequent processing modules, a recruitment device (19) of empty child test tubes (2), marking and loading devices (3) of empty child test tubes (2) into empty transport devices (8) stocked in said first lane (9), a device (4) suitable for the withdrawal and distribution of portions of biological material from the parent test tube (1) to the respective child test tubes (2) queued to the idle parent test tube (1) at the work point (11) of the work bench (5), a recruitment and loading device (22) of pipettes (23) suitable for the withdrawal of portions of biological materials and their distribution in child test tubes (2), and a control unit (100) suitable to coordinate and check the devices involved in the work cycle of the described device.

3 Claims, 13 Drawing Sheets

ALIQUOTING APPARATUS FOR BIOLOGICAL MATERIAL CONTAINERS

The present invention concerns an apparatus for the withdrawal and distribution of portions of biological materials from a parent test tube transported by an automatic plant for transporting child test tubes, marking and unloading the same from the automatic transport plant towards further processing modules.

The development of Laboratory Medicine observed over the past twenty years has induced test laboratories to promote the use of machinery aimed at automating laboratory tests, obtaining various advantages, such as speeding up tests and increasing safety for laboratory operators who, needing only to manage machinery, are increasingly less involved in directly handling potentially infected biological materials to be tested.

The creation of an automatic working chain, which may comprise the various steps of processing the biological material (preparation, testing and possible preservation) is now an increasingly common requirement in all medium to large-sized test laboratories where large work loads are dealt with everyday.

An automatic working chain means a set of devices for processing biological materials, comprising a conveyor belt suitable for presenting the biological material containers to said devices, managing the processing and storing the life cycle thereof.

There is obviously the need to ensure equal efficiency in each step of the working chain in order to prevent "bottle-necks" which could cause hold-ups in biological material specimen processing, and thus limit the great advantages deriving from introducing the automatism.

Possible hold-ups may be caused because various types of tests generally need to be carried out on the same specimen contained in a single test tube.

The analyzers suitable for carrying out the required tests on the specimen are not always all connected to the automation chain, but in some cases may be located in different areas of the same laboratory, and sometimes even in different laboratories.

Therefore, in order to complete the required tests on a biological material specimen, the specimens must often be transported close to the analyzers, thus considerably increasing the times of processing said specimen.

In order to decrease these wastes of time as much as possible, the specimen may be aliquoted, which consists in portioning the same, from the original test tube, named parent, into several test tubes, named children, thus containing portions of the original biological material specimen.

Thereby, the tests to be carried out on the specimen may be carried out in parallel, thus reducing the waiting times and also obtaining a high number of tests on the same specimen in a short time.

However, the benefits deriving from portioning a biological material specimen into a given number of children test tubes may be limited by the fact that this process, normally carried out by hand, leads to further handling by the operator, which could cause delays, hold-ups and errors in identifying the new containers containing the original biological material parts.

It is the object of the present invention to provide analysis laboratories with specifically automated, mutually integrated devices serving the function of drawing part of the biological material contained in a parent test tube and portioning it into a number of child test tubes, depending on the type and amount of processes needed on said biological material, prudently and univocally marked so as to overcome the drawbacks mentioned above.

In accordance with the invention, the object is achieved by an automatic apparatus suitable for the withdrawal of portions of biological material from a parent test tube, mobile in a conveyor of a test tube transport plant by means of transport devices of single test tubes, to be loaded in one or more child test tubes countermarked beforehand with suitable identification means and to be sent to different biological material analysis instruments interfaced to said transport plant, characterized in that it includes a work bench which provides a first lane for stocking and filling of transport devices with empty child test tubes, a second lane for stocking parent test tubes, said lanes being selectively joined in such a way to consent the sending of single parent test tubes with a predefined number of child test tubes subsequently assigned to be filled of biological material drawn from the parent test tube in a work point, and a return third lane of parent test tubes and child test tubes filled with portions of biological material drawn from parent test tubes, said lanes joining to a conveyor suitable for the transport of test tubes to and from subsequent processing modules, a recruitment device of empty child test tubes, marking and loading devices of empty child test tubes into empty transport devices stocked in said first lane, a device suitable for the withdrawal and distribution of portions of biological material from the parent test tube to the respective child test tubes queued to the idle parent test tube at the work point of the work bench, a recruitment and loading device of pipettes suitable for the withdrawal of portions of biological materials and their distribution in child test tubes, and a control unit suitable to coordinate and check the devices involved in the work cycle of the described apparatus.

The conveyor comprising the interface area serves the function of presenting the parent test tubes to be aliquoted, transport devices to be loaded with child test tubes and conveying, at the end of the working cycle, the aliquoted test tubes and children test tubes toward further processing modules.

The marking and loading device of children test tubes ensures a suitable supply of children test tubes, if required during the process.

The device suitable for withdrawing and distributing biological material from parent test tubes to previously marked children test tubes could be a mechanical arm provided with disposable needle or pipette suitable for drawing a predetermined amount of the biological material contained in the parent test tube and for distributing said material into the children test tube(s) so that such a material may be distributed in previous established equal or different amounts.

Said device may be integrated with a further device adapted to supply the disposable pipettes.

The device object of the invention must be capable of coordinating the devices it consists of and running operations in parallel so as to optimize the working cycle. In order to obtain this, a control unit is included, which may be a software application residing on a computer and suitable for receiving information and sending commands to the operating devices.

The advantages obtained by using an automatic device for withdrawing and dispensing material into specifically marked, children test tubes connected to an automatic transporting system are the following:

optimizing working flow and increasing process efficiency;

optimizing times and reducing waste;

optimizing use of personnel;

maximum quality and safety;

ensuring test tube pre-post testing process traceability (by virtue of specific marking);

reducing human error associated with manual sample processes;

reducing the exposure of personnel to biologically dangerous material.

These and other features of the present invention will become more evident from the following detailed description of a practical embodiment thereof, shown by way of non-limitative example in the accompanying drawings, in which.

Figure 1:
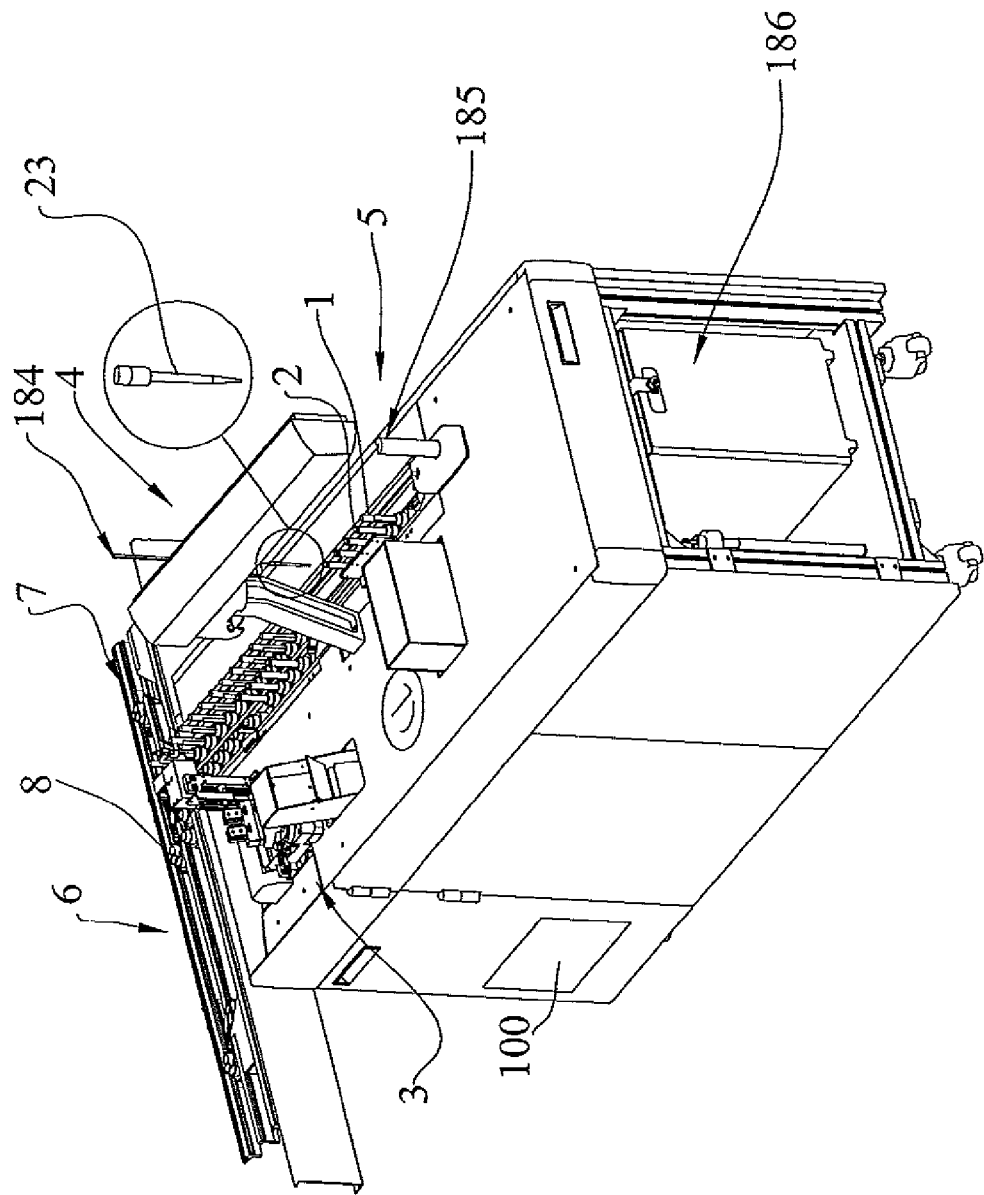
FIG. 1 is a perspective view of the aliquoting apparatus.

FIG. 1 shows an aliquoting or portioning apparatus of biological material from parent test tubes 1 into children test tubes 2 according to the present invention, comprising a marking and loading device 3 of children test tubes 2 and a withdrawal and distribution device 4 of biological material.

Said devices 3 and 4 interface with a work area or bench 5 connected to a conveyor 6 of a transport plant of test tubes to and from processing and testing modules. Such a conveyor 6 consists of a conveyor belt 7 (FIGS. 1 and 2) organized in lanes and suitable for conveying the test tubes to the interface points with processing modules.

The conveyor 6 uses test tube transport devices or carriers 8, suitable for containing the test tubes in a vertical, firm position and further stopping and diverting devices.

The work area 5 (FIG. 2) comprises a lane 9 adapted to receive empty transport devices 8 from the conveyor 6, which are queued in said lane 9 waiting for being loaded with children test tubes 2 by the marking and loading apparatus 3, a lane 10 suitable for presenting conveying devices 8 containing parent test tubes 1 close to the work point 11 of the biological material withdrawal and distribution apparatus 4, a return lane 12 of parent test tubes 1 and children test tubes 2 filled with aliquots or portions of biological material contained in the parent test tube.

Close to the work area 5, the conveyor 6 has a main lane 13 (FIG. 2), a diversion 14 adapted to convey empty transport devices 8 into a secondary lane 130 and thus into the lane 9, a diversion 15 after diversion 14 suitable for conveying transport devices 8 containing parent test tubes 1 of the lane 10.

The various devices included in the aliquoting apparatus are coordinated during the operations, according to the history and identity of the parent test tubes presented in the work area 5, by a control unit 100 (FIG. 1), consisting of a software program installed on a personal computer communicating with a code residing on one or more electronic boards suitable for the handling of the involved devices.

The identity of a parent test tube 1, let into lane 10 close to the deviation 15, is communicated by the control unit 100 to the marking and loading apparatus 3, starting the preparation of child test tubes and ensuring the univocal association with the parent test tube from which the biological material aliquots are extracted.

The child test tubes may also be marked without providing for any association with the original parent test tube; this depends on the test laboratory request only. The information to be included in the children test tube marking may be thus configured, according to the laboratory, in the software which manages the marking during installation of the apparatus in the laboratory.

The parent test tube is parked in a stop point 16; when the children test tubes are appropriately marked, positioned in the lane 9 and queued in a stop point 106, the parent test tube 1 is released from the stop point 16 to reach the work point 11, followed by the children test tubes, which are released and queued after the parent behind the work point 11, passing from lane 9 to lane 10 through the diversion 17. The actual presence of the expected number of children test tubes 2 queued after the parent test tube 1 in the work point 11 is controlled by presence sensors 18 appropriately positioned on lane 10.

The number of children test tube to be prepared depends on the type of processing required on the biological material contained in the parent test tube 1.

The marking and loading apparatus 3 (FIG. 3) comprises a test tube recruitment device 19, adapted to present children test tubes 2 to a marking device 20; at the end of this operation, the appropriately countermarked children test tubes 2 are positioned in transport devices 8 by a test tube handling device 21.

The marked children test tubes 2 positioned in the transport devices 8 are then queued, as previously explained, to the parent test tube 1 in the work point 11.

Figure 11:
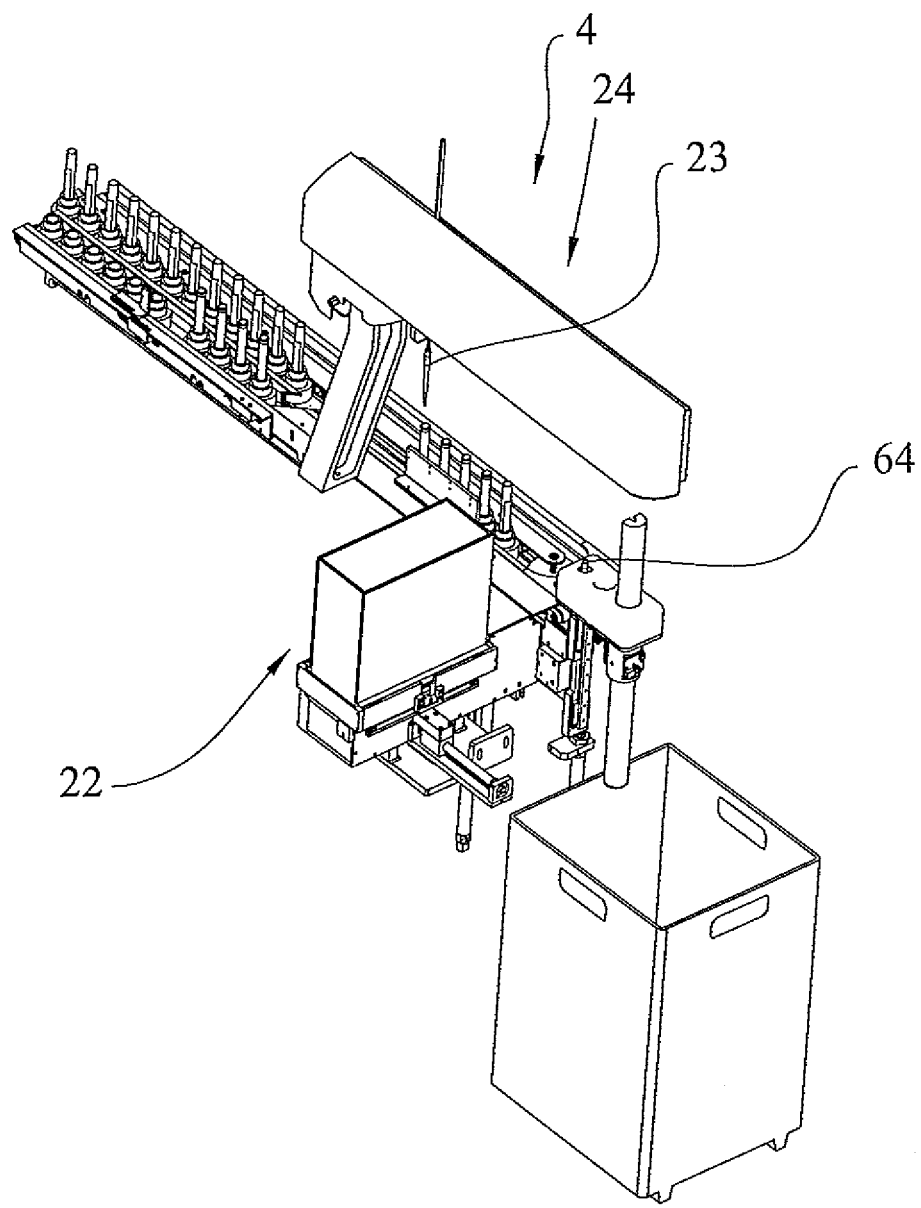
FIG. 11 is a perspective view of the withdrawal and distribution device.

Said work point 11 is the work area of the withdrawal and distribution apparatus 4 (FIG. 11), which comprises a recruitment device 22 of pipettes 23, having the function of presenting a pipette 23 in an appropriate position at each new work cycle. Said pipette 23 (FIG. 1) is a tubular body, equivalent to a pipe, which is adapted to aspirate the biological material contained in the parent test tubes.

The pipette 23, recruited by the recruitment device 22, is then engaged and automatically mounted and interlocked on a biological material distribution device 24, as will be explained below. The reason why the pipette for drawing biological material from the parent test tube 1 is changed at each cycle is to avoid risks of contamination between biological materials belonging to different test tubes.

The steps of an aliquoting cycle are described below:

a parent test tube 1 to be aliquoted contained in a specific transport device is present on the main line 13 of the conveyor 6, the conveyor 6 diverts such a test tube to lane 10 through diversion 15 to allow the test tube to reach the work area 5, the parent test tube 1 is stopped by a stop device in waiting point 16, according to the identify of the parent test tube 1 (known beforehand) and the processing which must be carried out on the biological material contained therein, the control unit 100 controls the marking and loading apparatus 3 for preparing a given number of children test tubes (in the example, the children test tubes are 4), the marking and loading device 3 thus prepares the required number of children test tubes, marking them and positioning them in the transport devices 8 available and queued in lane 9, the parent test tube 1 idle in the stop point 16 is released to reach the work point 11, having reached the point, the children test tubes 2 queued in lane 9 are released through diversion 17 to be queued after the parent test tube in lane 10, a new pipette 23 is recruited by the pipette recruitment device 22 ad positioned in point 64 in which it must be engaged by the distribution device 24 to start the biological material withdrawal operation, the distribution device 24 which withdraws the biological material from the parent test tube 1 at the top of the list, the presence sensors 18 check that the number of children test tubes 2 queued after the parent test tube 1 is the expected one, the biological material taken by the distribution device 24 with the pipette 23 is distributed in the queued children test tubes, the parent 1 and children test tubes 2 are released onto return lane 12 to go back to the main line 13 of the conveyor 6 and may be transported to subsequent processing or analysis modules.

The test tube recruitment device 19 (FIG. 4) consists of fixed combs 25 and mobile combs 26. The mobile combs 26 move (as shown by the arrows in FIG. 4) on fixed combs 25 engaging the test tubes, contained in a hopper 101 (FIGS. 3 and 5), and moving them upwards.

Figure 3:
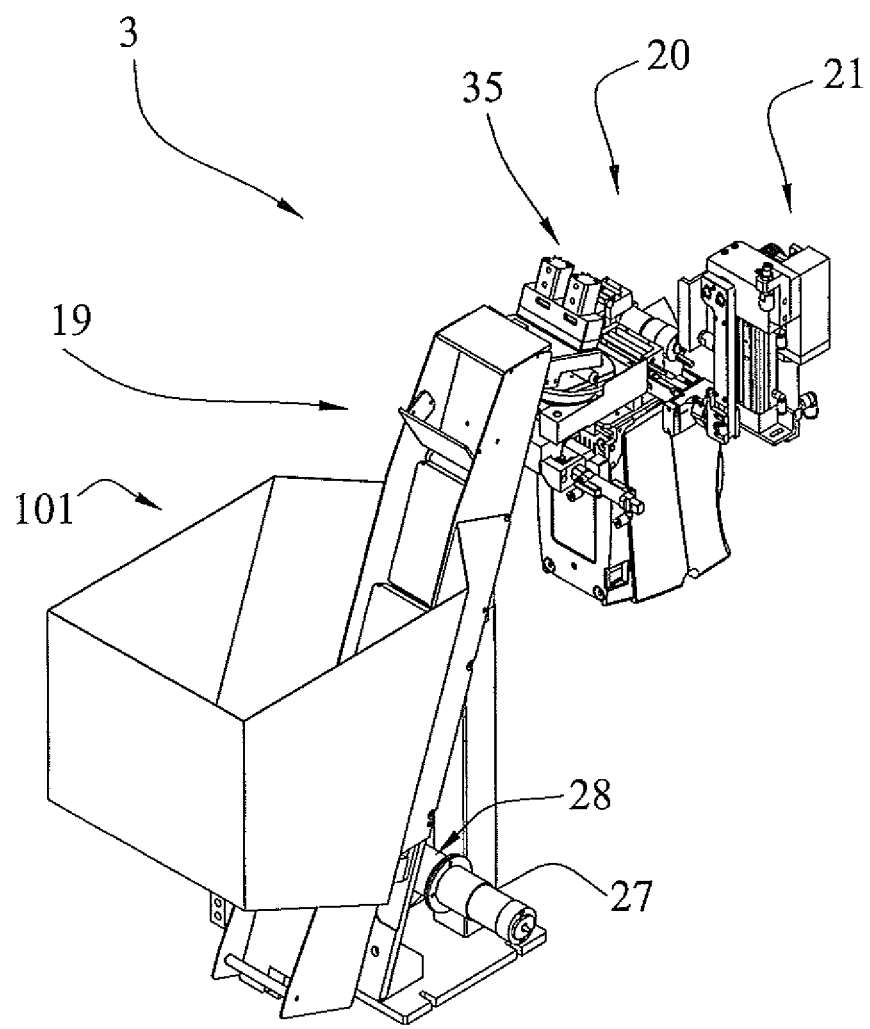
FIG. 3 is a perspective view of the marking and loading device.
Figure 4:
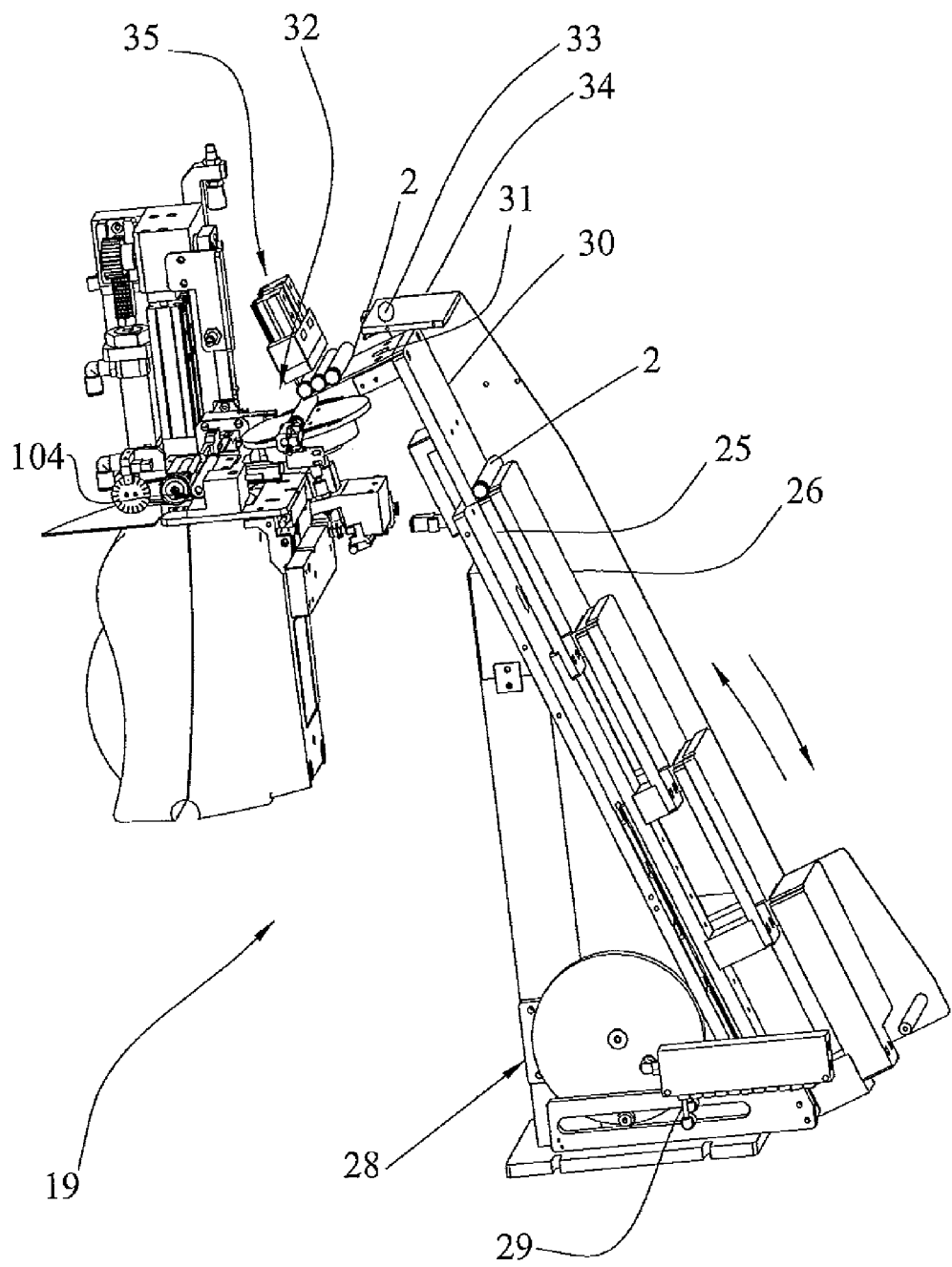
FIG. 4 is a front view of the marking and loading device with some covers and the hopper being removed.
Figure 5:
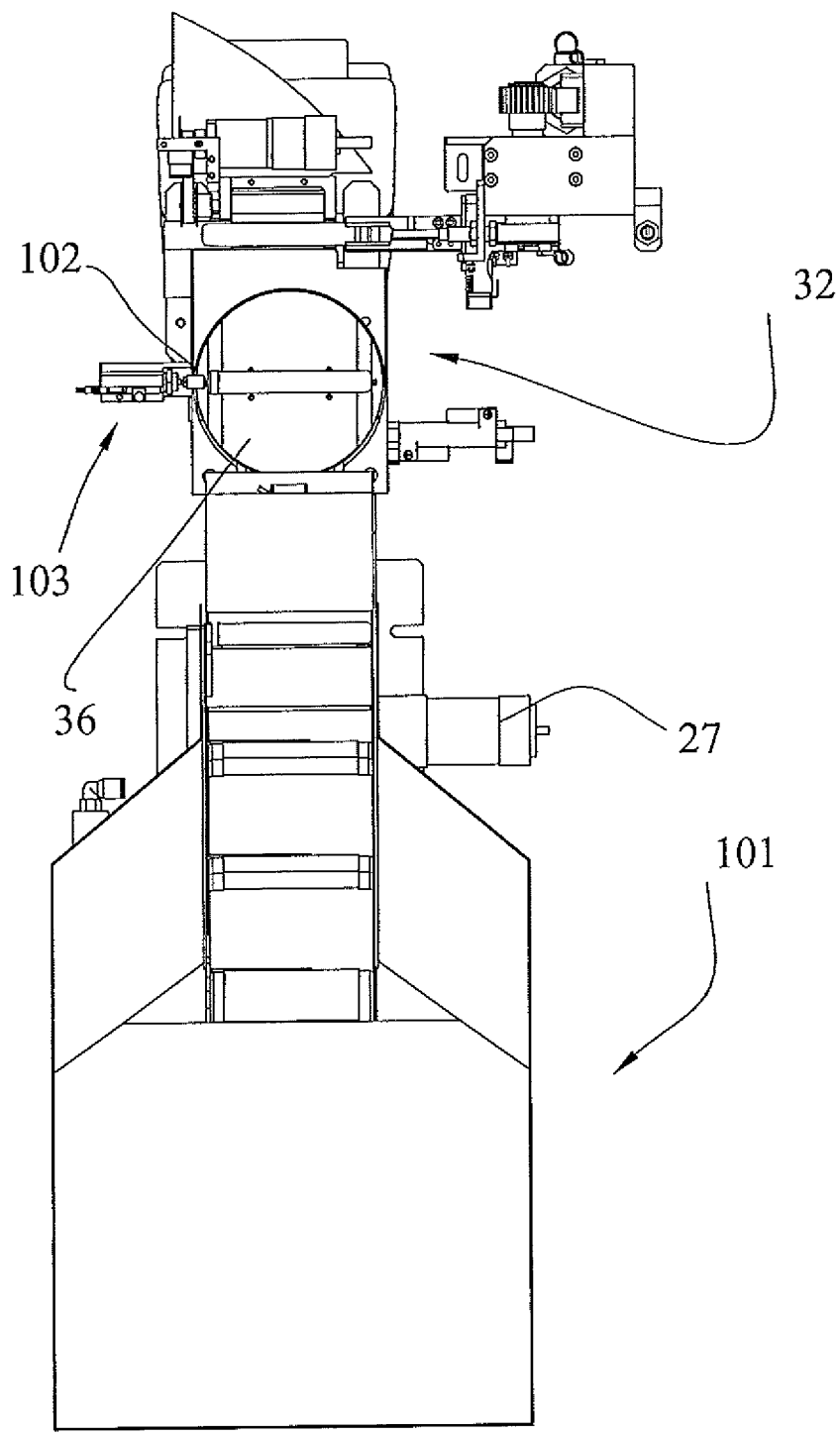
FIG. 5 is a top plan view of the configuration in FIG. 3.

The mobile combs 26 are moved by an electric motor 27, which, by means of a transmission system 28, moves a mobile arm 29, generating the travel of the mobile combs 26 on the fixed combs 25 (FIGS. 3, 4 and 5).

Figure 6:
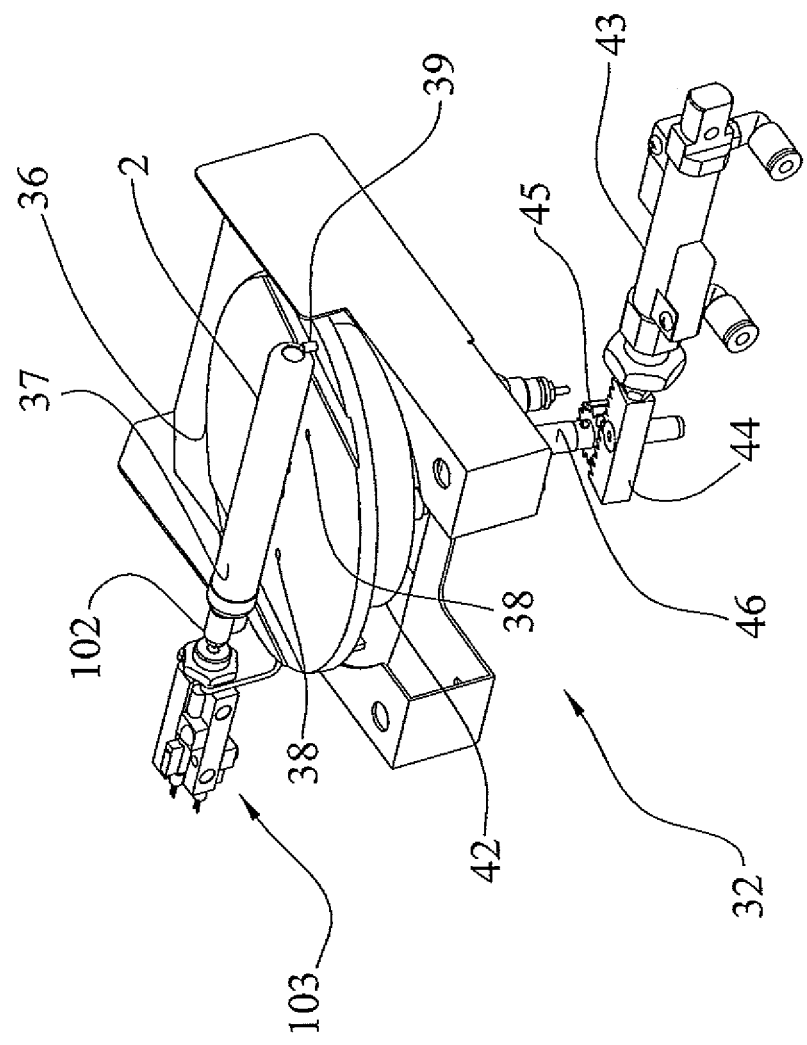
FIG. 6 is a perspective top view of the test tube revolving device.

A test tube engaged by such a mechanism reaches the fixed test tube 30 (FIG. 4) positioned in the highest position, slides on an inclined tray 31 falling onto a test tube revolving device 32 (FIG. 6). Said tray may accommodate up to 8 test tubes; a presence sensor 33 (FIG. 4) on the cover 34 of the tray 31 has the task of checking the actual presence of the eighth test tube on the tray and possibly stop the operation of the test tube recruitment device 18 to disposal of the 8 test tubes.

A pneumatically operated test tube timer 35 is over the tray 31 (FIGS. 3 and 4) for checking that the test tubes fall on the revolving device 32 one at a time.

Said test tube revolution device 32 (FIG. 6) comprises a revolving dish 36, which includes a lodging 37 consisting of four cylindrical retractable pegs 38 (two of which are not shown in FIG. 6 because they are hidden by the body of the child test tube 2) and a fixed cylinder pin 39 in which the test tube falling from the tray 31 is engaged.

A cylinder 103 (FIG. 6) works as sensor, detecting the position of the test tube on the revolving dish 36: when the test tube is in the lodging 37 said cylinder 103 is actuated and a piston 102 consequently exits.

By detecting the exit of said piston 102 from the cylinder 103, distinguishes the following two events:

if the piston enter inside the test tube, it means that the open end of the test tube is facing the side of the sensor (as shown in FIGS. 5 and 6);

if the piston does not enter, it means that the closed end of the test tube is facing the side of the sensor, thus preventing the entrance of the piston therein.

In this case, the test tube may be released by the dish 36; in the first case, instead, the dish turns by one-hundred-eighty degrees to take the test tube to the desired position.

Figure 7:
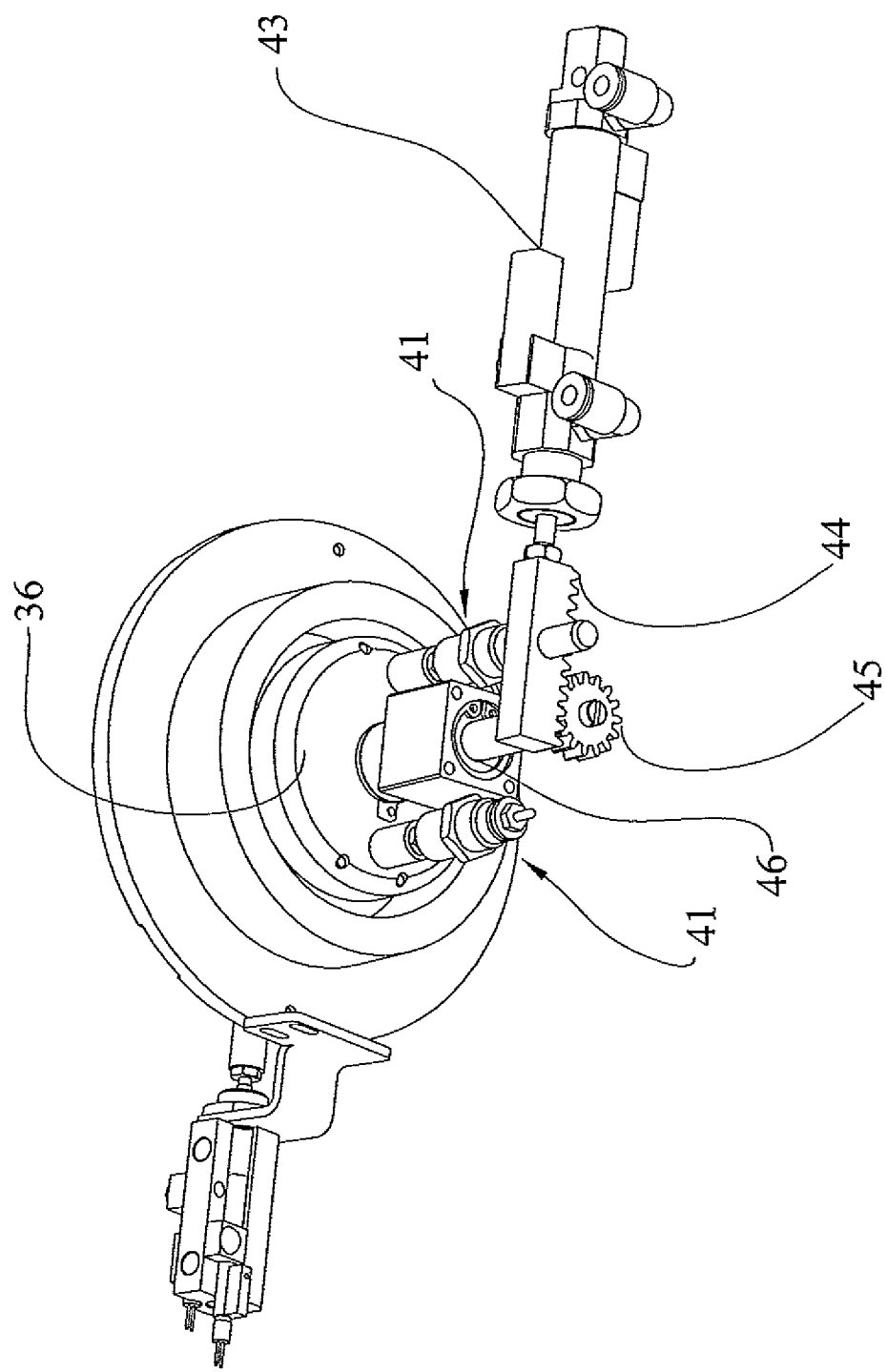
FIG. 7 is a perspective bottom view of the configuration in FIG. 6.
Figure 8:
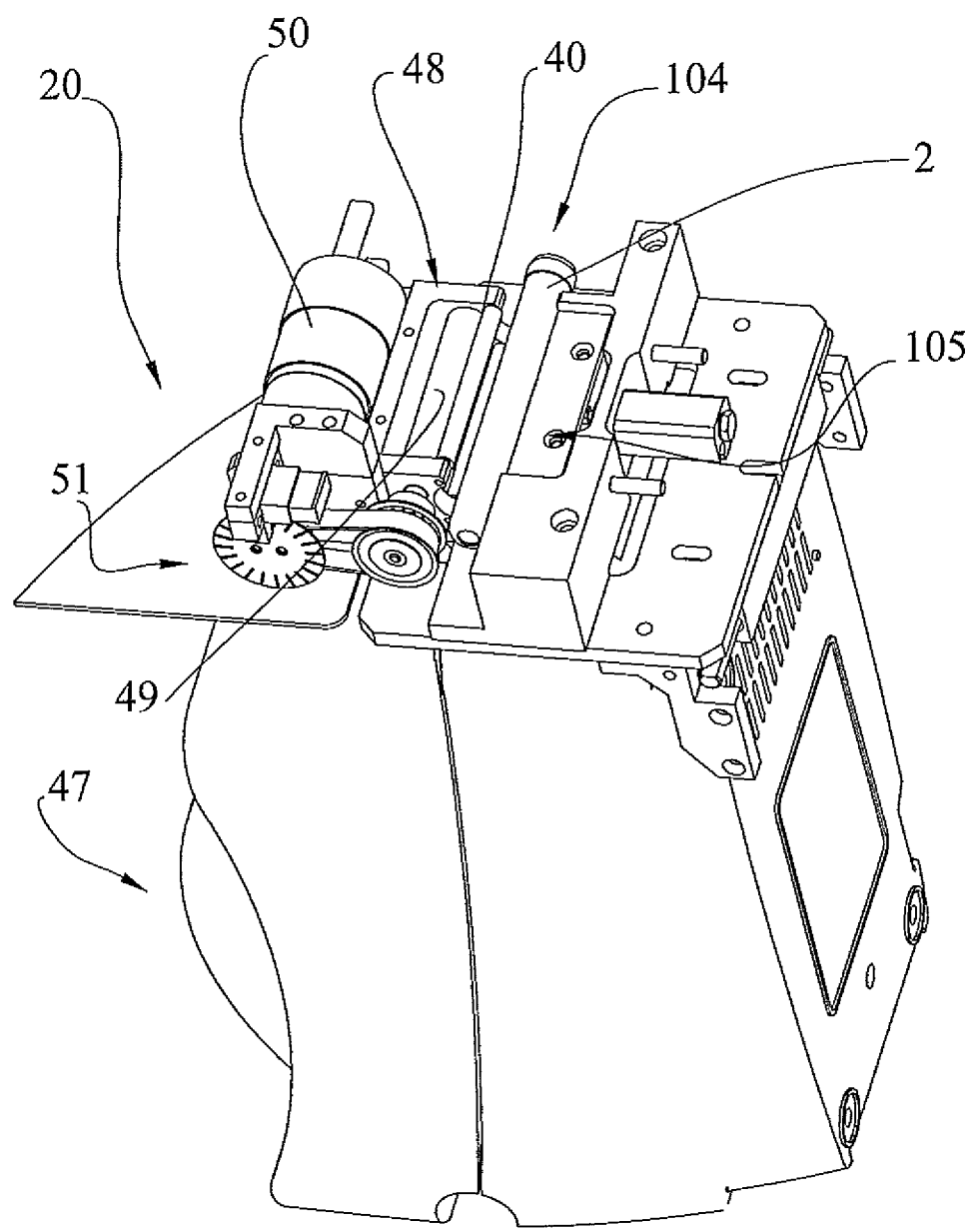
FIG. 8 is a perspective view of the test tube marking device.

When said position is obtained, the two pneumatic cylinders 41 (FIG. 7) retract the cylindrical pegs 38, allowing the release of the test tube into a lodging 104 comprising two rollers 40 (FIGS. 4 and 8, in FIG. 8 the second roller 40 is not visible because it is hidden by the body of the test tube 2 positioned in the lodging 104).

The dish 36 (FIGS. 6 and 7), included in a lodging 42, is inclined with respect to the horizontal to allow the test tube, when released from the cylindrical retractable pegs 38 to roll inside the lodging 104. A cylinder 43 generates the rotation of the plate 36. The linear movement generated by said cylinder 43 is transformed by virtue of a transmission system comprising a rack 44 which by engaging a gear 45 moves a shaft 46, which generates the rotation of the plate 36 in the lodging 42, when required.

The test tube marking device 20 (FIG. 8) comprises a label application device 48 adapted to ensure the adhesion of said adhesive labels onto the side walls of the child test tube 2 positioned in the housing 104. These adhesive labels are printed by a printer 47.

After having reached the shaft 104 according to the correct orientation a sensor 500 (positioned in the lodging 104 under the test tube and not visible in FIG. 8) confirms the presence of the child test tube 2, operating the label printer 47 which produces a label containing useful information for identifying the child test tube 2 during the subsequent steps of processing on the conveyor 6 and, if required, associates the identity to the parent test tube.

Said label, exiting from the printer 47, is engaged between the rollers 40 and, being adhesive on one side, is glued onto the wall of the test tube.

The label application device 48 has the function of making sure that the label sticks to the side wall of the test tube. It comprises an active roller 49, the rotation of which generates the rotation of the two rollers 40, actuated by an electric motor 50 the movement of which is transmitted to the roller 49 by a transmission system 51.

Further rollers may be present in a loading 105 in order to ensure a better revolution of the test tube while the label is being glued.

The revolution of the rollers is sufficiently long to ensure the adhesion of the label onto the side wall of the test tube.

The correctly marked child test tube 2 is ready to be loaded into a transport device 8 in lane 9 positioned in a release point 63 (FIG. 2) by the test tube handling device 21.

Figure 9:
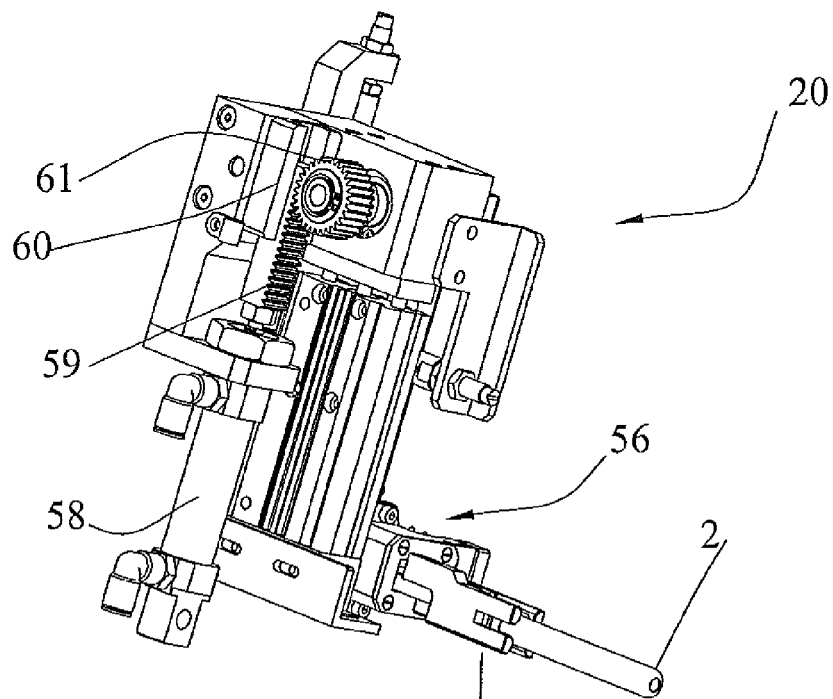
FIG. 9 is a perspective left side view of the test tube handling device.
Figure 10:
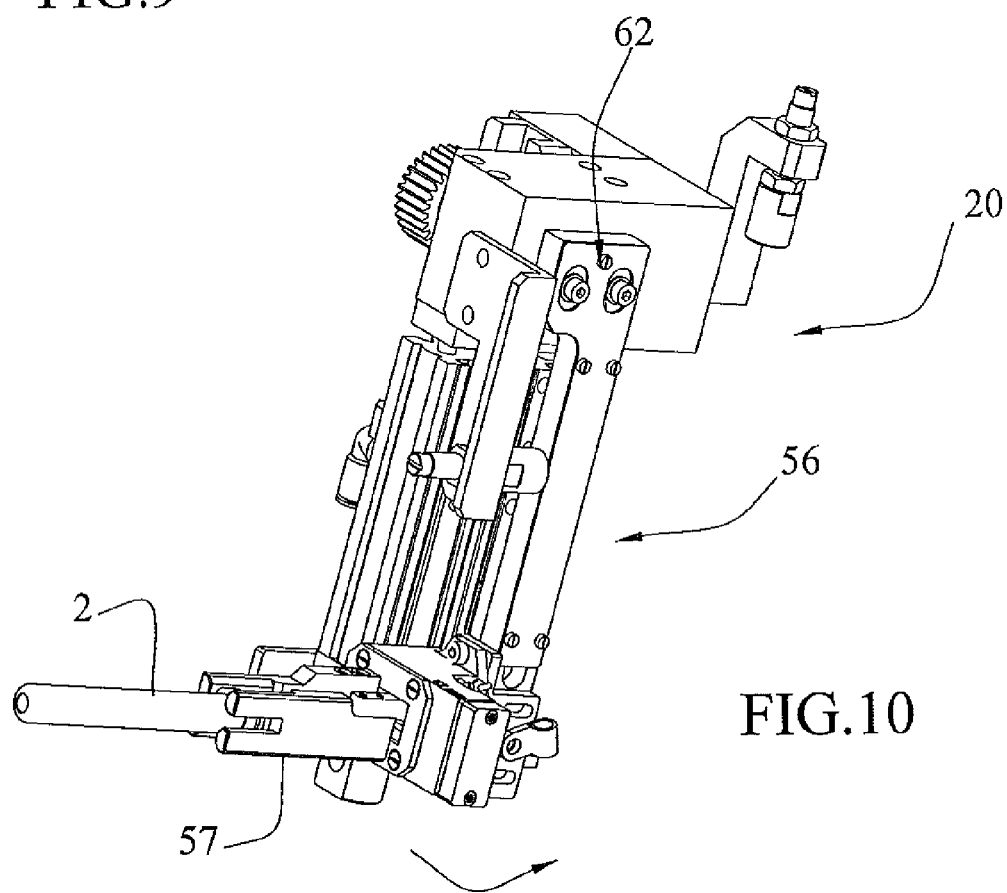
FIG. 10 is a perspective right side view of the configuration in FIG. 9.

Said test tube handling device 21 (FIGS. 9 and 10) consist of a mechanical arm 56 comprising a gripper 57 capable of gripping the test tube, as shown in the FIG. 9, and turning on the pins 62, reaches the release point 63 following the direction of revolution shown by the arrow in FIG. 10.

The revolutionary movement of the mechanical arm is obtained by transforming the linear movement of a cylinder 58 by means of a rack 59 contained in a guide 60 on which a circular gear 61 turns.

The gripper 57, after having reached the release point 63 opens pneumatically and releases the test tube, inserting it in an empty transport device 8 idling in the release point 63.

Figure 2:
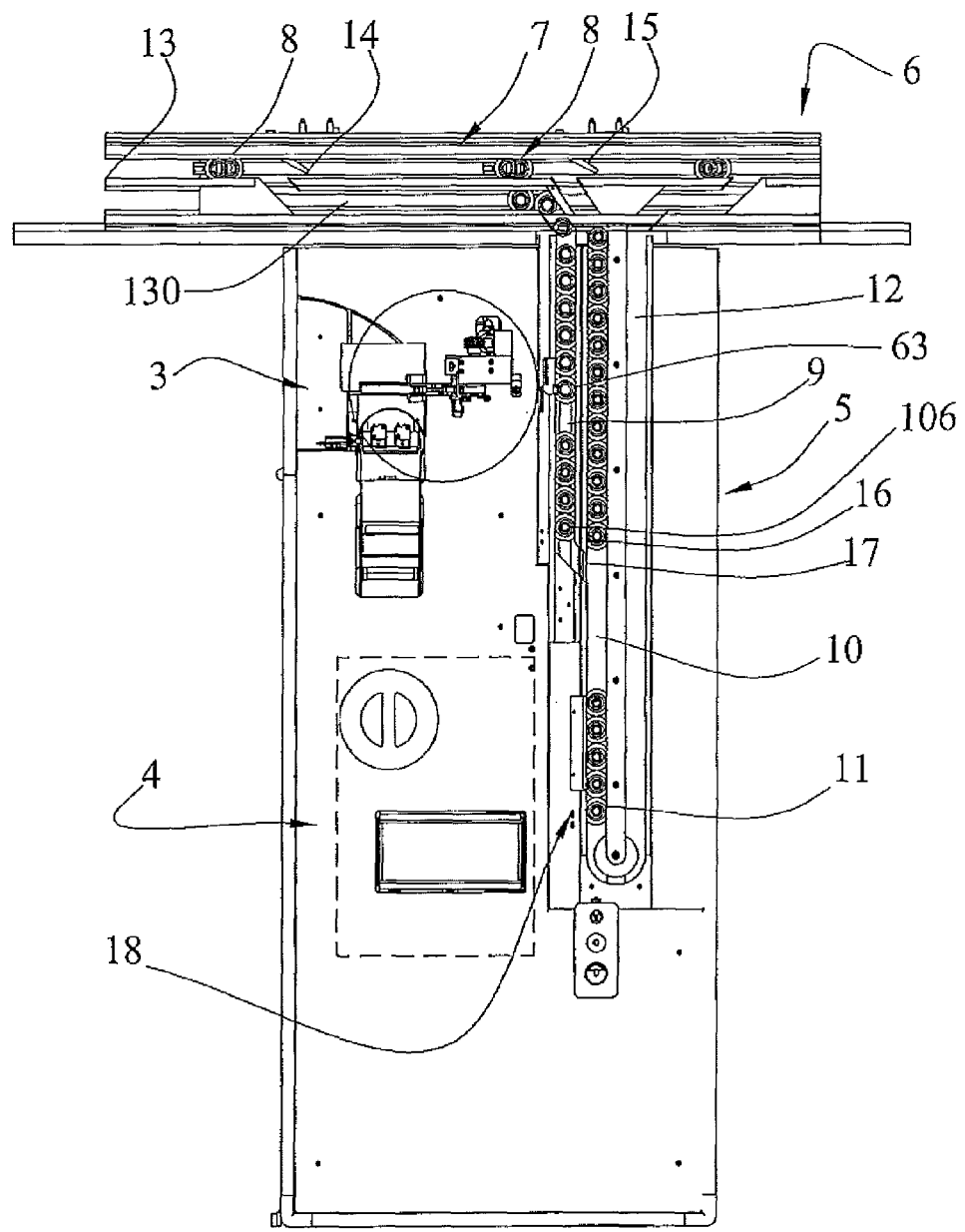
FIG. 2 is a top plan view of the configuration in FIG. 1 in which the withdrawal and distribution device is shown with a dashed areas for simplicity.

If several children test tubes are needed for one parent test tube, a child test tube ready in its transport device 8 is released from the release point 63 and queued in the stop point 106; the described process is repeated and when all the children test tubes 2 are correctly positioned in the corresponding transport devices 8 queued in stop point 106, are conveyed from lane 9 to lane 10 and queue after the parent test tube positioned in work point 11 (FIG. 2).

In such a work point, the biological material withdraw and distribution device 4 (FIG. 11) has the task, after having acquired a new pipette 23 from the spare pipette position 64, to draw a specimen of biological material from the parent test tube 1 at the top of the queue and distribute it into the queuing children test tubes 2.

A pipette 23 is prepared in the spare pipette position 64 by means of the pipette recruitment device 22 (FIG. 12), comprising a pipette positioning device 65 and a pipette raising device 66.

Figure 13:
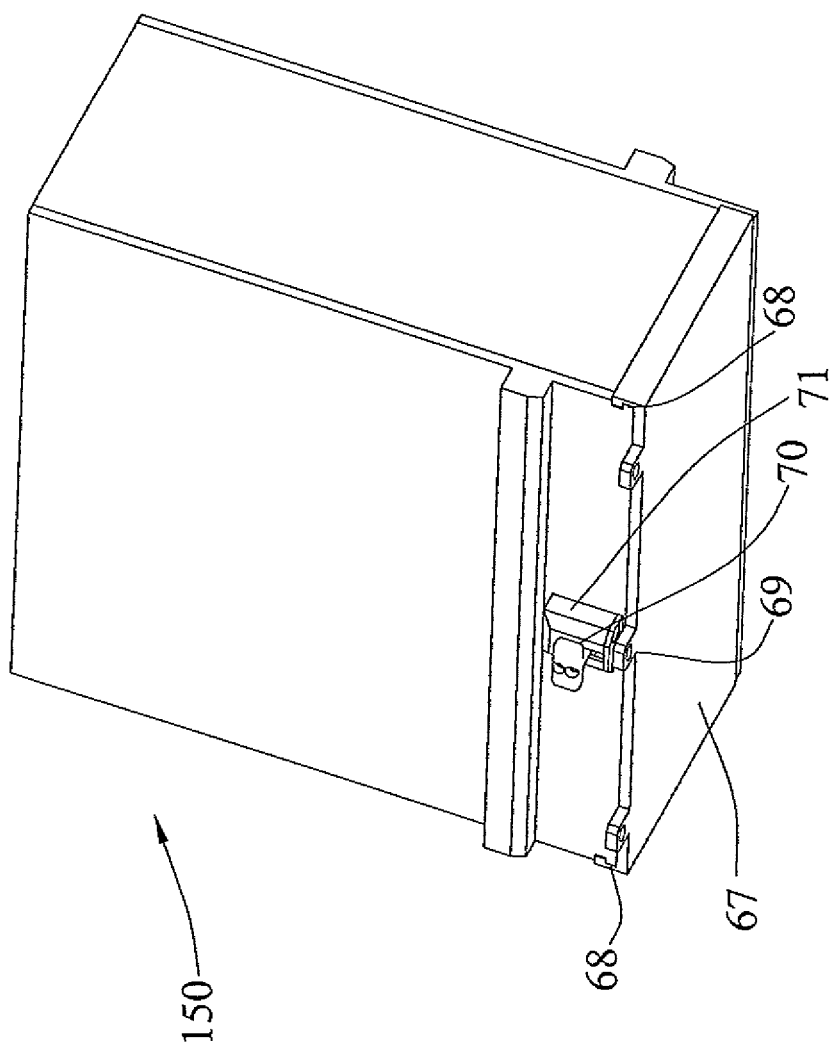
FIG. 13 is a perspective bottom view of the pipette container.

The pipettes are recruited by a container 150 (FIG. 13) which, for a greater process efficiency, must be loaded with the pipettes positioned in a horizontal direction; it consists of a lower base 67 removable by sliding along guides 68 and comprising a coupling 69 suitable to be engaged by a sliding hook 70 accommodated in a guide 71 positioned on the side wall of the container 150.

The pipettes are separately loaded into the container 150; subsequently, the container is fitted on the recruitment device 22; when correctly positioned in its seat, a support 73 couples with the hook 70 causing the lifting and consequent uncoupling from the coupling 69, which is immediately coupled by a second hook 74 (not shown in FIG. 12) mounted on a slides 75. Said slider 75, by sliding on a cylinder 76, removes the lower base 67 allowing to open the lower part of the container 150.

Figure 12:
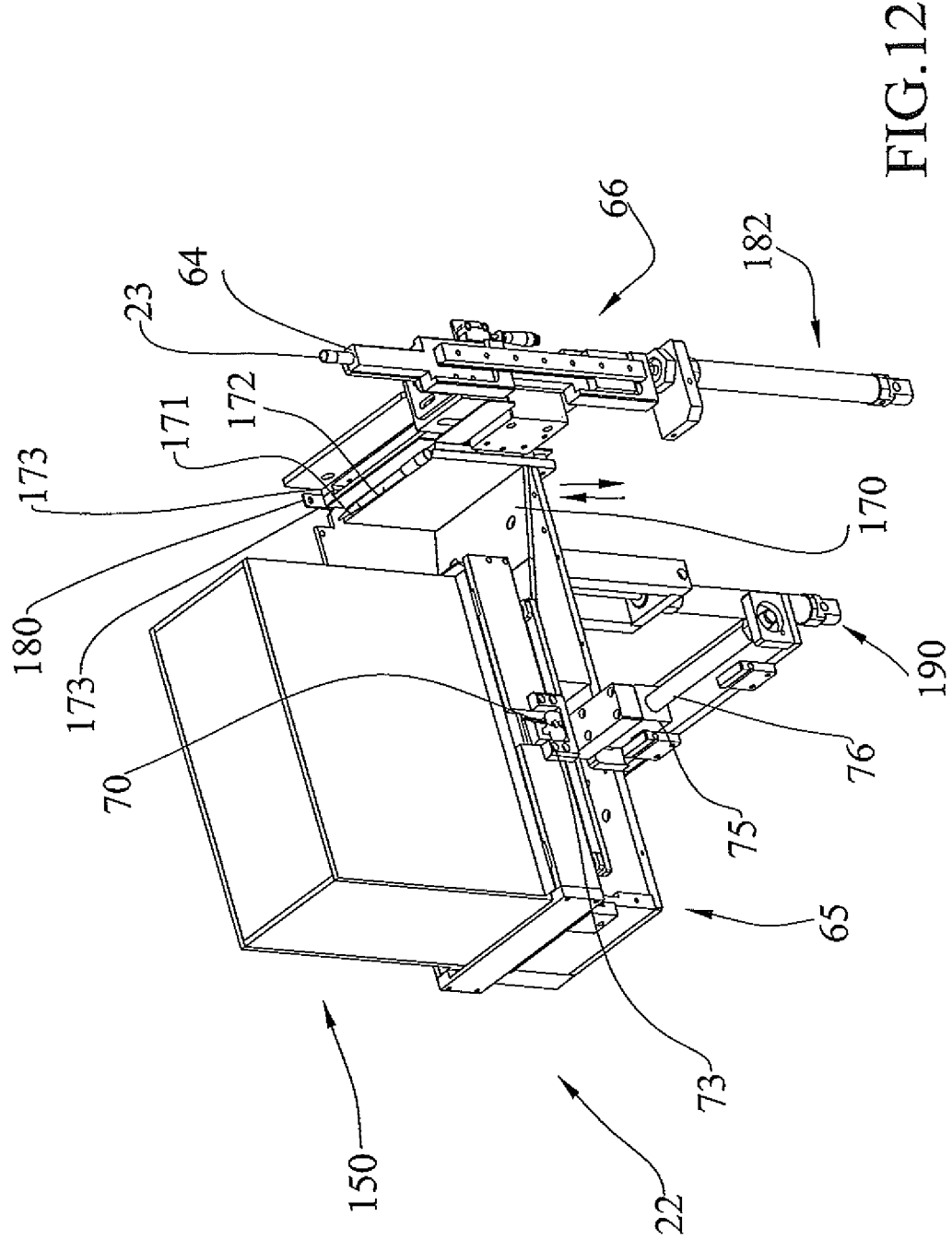
FIG. 12 is a perspective view of the pipette recruitment device.

The pipettes, thus released, fall on an inclined surface 170 mobile in a vertical direction (from the bottom upwards and vice versa as shown by the arrows in FIG. 12), where a comb 171, integrally mobile with the inclined surface 170, recruits the pipettes one by one, lifting them to the height of a chute 172.

The vertical movement of the inclined surface 170 and of the comb 171 is generated by a piston 190.

On said chute 172, the pipettes roll until they reach two guides 173 positioned at reciprocal distance equal to the width of the lower part, the thinnest, of the pipette (enlargement in FIG. 1). Said distance allows the pipette to "straighten up" when its reaches it remaining suspended on the edges of the two guides resting on the head which is wider than the body.

Figure 14:
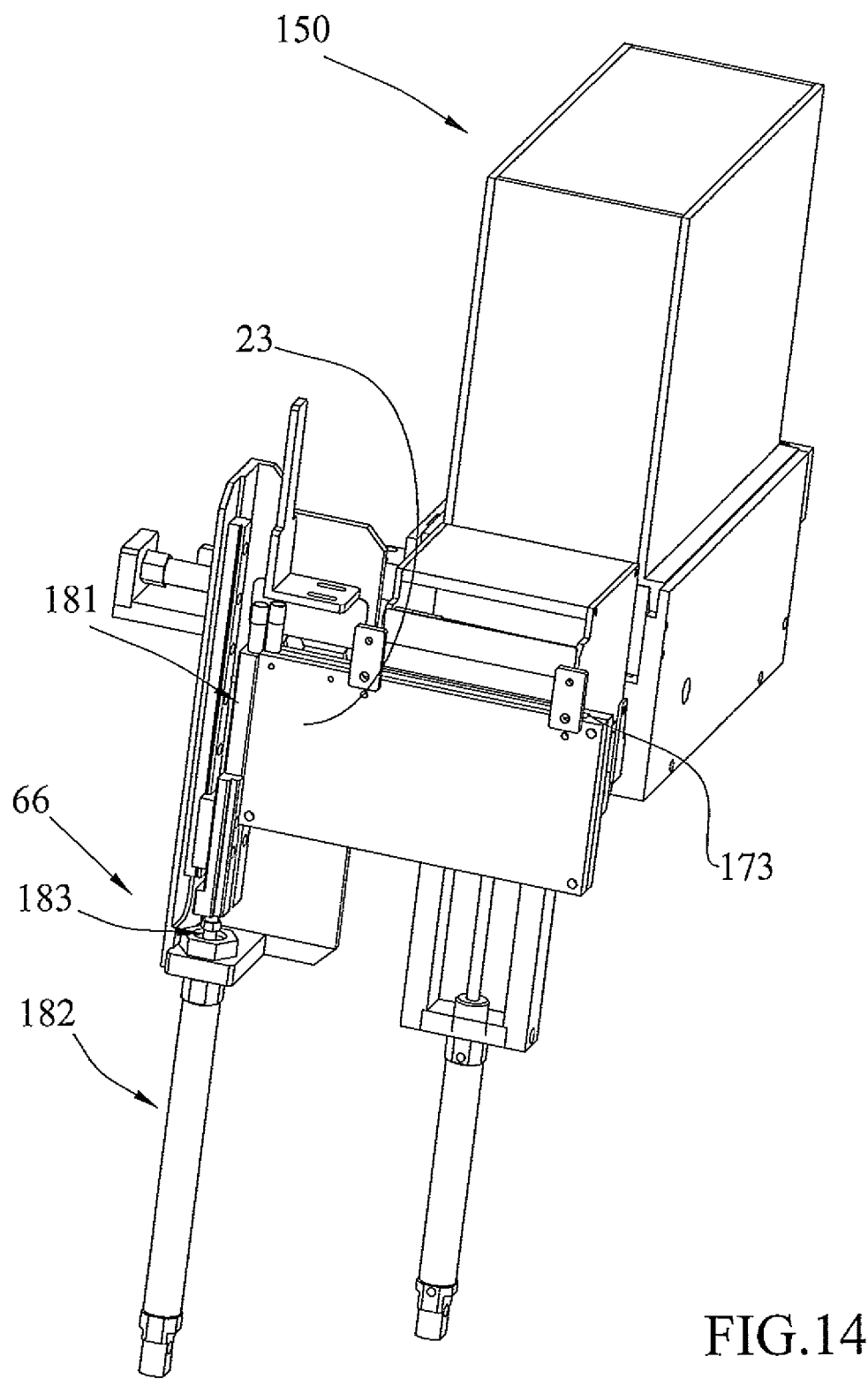
FIG. 14 is a perspective view of the pipette raising device.

A pushing system 180, consisting of for example a solenoid valve adapted to generate a jet of air in the direction of the pipette 23 positioned on the two guides 173, generates the movement of said pipette in the direction of a chamber 181 present inside the test tube lifting device 66, as shown in FIG. 14.

The pipettes 23, thus queued in this position, are pushed upwards, to reach the spare pipette position 64 (FIG. 12) by a pusher 183 moved by means of a piston 182.

When the distribution device 24 needs to replace a used pipette with a new one to start a new aliquoting cycle, a mechanical arm 184 suitable for handling the pipette, is positioned in a reject tube 185 (FIG. 1), where the pipette inserted inside said tube, is disengaged by the mechanical arm 184, falling in a pipette reject container 186.

At this point, the mechanical arm is positioned in the spare pipette position 64 and may engage a new waiting pipette.

The invention claimed is:

1. An automatic apparatus suitable for the withdrawal of portions of biological material from a parent test tube, mobile in a conveyor of a test tube transport plant by means of a transport device of single test tubes, to be loaded in one or more children test tubes which have been countermarked beforehand, which comprises:

a work bench which provides a first lane provided with a stop point for queued children test tubes, a second lane provided with a stop point for queued parent test tubes, a return third lane for accommodating parent test tubes and children test tubes filled with aliquots or portions of biological material received from the parent test tube, said parent test tube being previously released from the stop point to reach a work point on the second lane, followed by a predefined number of children test tubes which were previously released and queued after the parent test tube, behind the work point passing from the first lane to the second lane through a diversion, the actual presence of the expected number of children test tubes queued after the parent test tube in the work point being controlled by the presence of sensors appropriately positioned at the second lane;

a device suitable for the withdrawal and distribution of portions of biological material from the parent test tube to the respective children test tubes queued to the parent test tube at the work point of the work bench;

a device suitable for presenting pipettes in an appropriate position at each new work cycle, and suitable for the withdrawal of portions of biological materials and their distribution in children test tubes; and a control unit suitable to coordinate and check the devices involved in the work cycle of the described device.

2. The apparatus according to claim 1, wherein a recruitment device for the child test tubes is interfaced with the work bench, said recruitment device comprising a test tube revolving device providing an inclined revolving dish including a lodging for a test tube constituted of retractable pegs and a fixed peg, a sensor suitable to detect the position of the test tube on the revolving dish and means suitable to operate the revolving dish in case the test tube does not face the prescribed side for the subsequent drop into a test tube marking device.

3. The apparatus according to claim 1, wherein the device suitable for presenting the pipettes comprises a comb suitable to raise, one by one, horizontal pipettes towards two guides spaced between them in such a way to cause the straightening of the pipette, and pneumatic pushing means suitable to raise the pipette towards a pipette loading position.

* * * * *